United States Patent [19]

McKeown et al.

[11] Patent Number: 5,512,271
[45] Date of Patent: Apr. 30, 1996

[54] SILICAS FOR USE IN TRANSPARENT TOOTHPASTE COMPOSITIONS

[75] Inventors: Ian P. McKeown, Aigburth; Peter W. Stanier, Elworth, both of England

[73] Assignee: Unilever Patent Holdings BV, Vlaardingen, Netherlands

[21] Appl. No.: 266,849

[22] Filed: Jul. 5, 1994

Related U.S. Application Data

[63] Continuation of Ser. No. 956,857, Oct. 2, 1992, abandoned.

[30] Foreign Application Priority Data

Oct. 2, 1991 [EP] European Pat. Off. ............... 91309047

[51] Int. Cl.$^6$ ............................. A61K 7/16; C01B 33/12
[52] U.S. Cl. ............................................ 424/49; 423/339
[58] Field of Search ............................... 423/339; 424/49

[56] References Cited

FOREIGN PATENT DOCUMENTS

| | | |
|---|---|---|
| 0139754 | 5/1985 | European Pat. Off. . |
| 0143848 | 6/1985 | European Pat. Off. . |
| 227334 | 7/1987 | European Pat. Off. . |
| 236070 | 9/1987 | European Pat. Off. . |
| 308165 | 3/1989 | European Pat. Off. . |
| 1482355 | 8/1977 | United Kingdom . |
| 1482354 | 8/1977 | United Kingdom . |

*Primary Examiner*—Raymond Henley, III
*Assistant Examiner*—William R. A. Jarvis
*Attorney, Agent, or Firm*—Cushman Darby & Cushman

[57] ABSTRACT

Amorphous silicas suitable for use as abrasives in transparent toothpastes can be prepared by a precipitation route. These silicas are distinguished by having a BET surface area of 100 to 450 m$^2$/g, a weight mean particle size of 5 to 15 microns, a plastics abrasion value of 16 to 26, a mean pore diameter from 2 to 12 nm, a transmission of at least 70% in the refractive index range from 1.430 to 1.443 and an oil absorption in the range from about 70 to about 130 cm$^3$/g.

11 Claims, No Drawings

SILICAS FOR USE IN TRANSPARENT TOOTHPASTE COMPOSITIONS

This is a continuation of application Ser. No. 07/956,857, filed on Oct. 2, 1992, now abandoned.

FIELD OF THE INVENTION

This invention relates to synthetic amorphous silicas, especially precipitated silicas, of use, for example, as abrasive agents in transparent toothpaste compositions.

BACKGROUND OF THE INVENTION

Toothpaste compositions are well characterised in the literature and many compositions are disclosed in patent specifications and other literature. Toothpaste compositions contain a number of specific components for example abrasive agents, fluoride sources, binders, preservatives, humectants, anti plaque agents, colouring agents, water, flavour and other optional ingredients. Of these components the abrasive agent is required to provide the appropriate cleaning and plaque removal without subjecting the tooth itself to excessive abrasion. Typically a toothpaste composition will contain from about 5% to about 50% preferably up to about 30% by weight of abrasive. Commonly used abrasives are aluminas, calcium carbonates and calcium phosphate. More recently synthetic silicas have been adopted because of their efficient cleaning, compatibility with other ingredients and their physical properties. An important property of a silica for use in transparent toothpaste formulations is its apparent refractive index, and the lower this value in the chosen water/humectant system the more water can be allowed for by the formulator in the transparent toothpaste. The replacement of the more expensive humectant, e.g. Sorbitol, by water leads to substantial cost savings.

The inventors have shown that the apparent refractive index of an amorphous silica can be controlled by the careful selection of process conditions in the preparation of silica. Changing these conditions alters the fundamental features of the overall pore size distribution present in the amorphous silica which in turn determines its apparent refractive index.

In particular, the extent of ultramicropores (below 0.7 nm diameter), which can preferentially adsorb water, when the silica is brought into contact with the humectant/water system, are thought to play a dominant role. Ultramicropores have been classified as pores which are small enough to exclude the nitrogen molecule (Characterisation of Porous Solids: An Introductory Survey—Kenneth SW Sing in Characterisation of POrous Soloids II 1991 Elsevier Science Publishers BV Amsterdam).

Prior Literature

Examples of precipitated silicas useful as toothpaste abrasives with low to medium structure can be found in GB 1482354 & GB 1482355 (Huber, EPA 0227334 & EPA 0236070 (Unilever), EPA 0143848 & EPA 0139754 (Taki). GB 1482354 and GB 1482355 disclose silicas for use in toothpastes in general but are silent on use in transparent toothpastes. EPA 0227334 and EPA 0236070 state in silicas as defined are not suitable for formulating into transparent toothpaste compositions.

EPA 0143848 and EPA 0139754 describe silicas with texture and apparent refractive index that can be used in transparent toothpastes. The patents disclose a process for the preparation of amorphous silicas with apparent refractive indices in the range 1.455 to 1.47, which in firing at 1100° C. yield a phase which is amorphous to x-rays, having BET surface areas in specified ranges. EP 0143848 discloses BET surfaces areas from of 270 to 500 $m^2/g$ and EP 0139754 discloses BET surface areas of from 5 to 60 $m^2/g$.

GENERAL DESCRIPTION OF THE INVENTION

The amorphous precipitated silicas for the invention provide a novel range of properties, combining high levels of abrasivity with good transparency at low apparent refractive index when incorporated into a dentifrice formulation. The levels of abrasivity obtained with the silicas of the invention are unusually high in view of the high degree of openness of structure the silicas possess as defined by oil absorption and porosity measurements. In particular, such high levels of abrasivity coupled with good dentifrice transparency at low apparent refractive index have not been obtained previously with precipitated silicas.

The silicas of the invention are capable of providing high levels of abrasion even at relatively low particle size, (i.e. 5 to 10 micron) and when the particle size distribution is closely controlled to eliminate coarse particles, particularly those greater than 30 µm. It is accepted that the abrasivity of an amorphous silica can be increased by broadening the particle size distribution to include larger percentages of particles in excess of 20 micron, however these materials can give rise to unacceptable mouth feel when formulated into toothpastes.

The silicas can be prepared with low levels of cations, e.g. calcium and magnesium, by washing the filtercake with de-ionised water such that the dry product subsequently gives extra stability when formulated into a toothpaste containing fluoride ions.

In general, characterisation of the pore structure of silicas containing higher levels of openness and wider pores by nitrogen adsorption techniques is not meaningful because the technique is useful only for pores up to about 60 nm diameter i.e. micropores (up to 2 nm) and mesopores (2–50 nm). To measure the full range of porosity present in such materials it is necessary to employ alternative procedures, for example oil absorption or mercury porosimetry. Since the products of this invention have considerable pore structure in excess of 60 nm i.e. macropores it is necessary to define them by means of such techniques.

Equally important in amorphous silicas is the presence of micropores (below 2 nm diameter 0 and in particular ultra-micropres (below 0.7 nm diameter) which cannot be detected by nitrogen adsorption measurements. The extent to which pores in this range dominate the micropore size distribution is shown by the shift in the apparent refractive index of amorphous silica when it is in contact with the humectant/water system. It has been postulated that the density of the amorphous silicas to Helium may give an insight to the presence of ultramicropores and these measurements have been utilised to further characterise the silicas.

The invention provides an amorphous silica, preferably a precipitated silica, having i) a BET surface area in the range from about 100 to 450 $m^2/g$, ii) a weight mean particle size in the range 5 micrins to 15 microns, with less than 10% of the weight particle size distribution greater than 20 microns, and preferably less than 5% greater than 25 microns, iii) a plastics abrasion value in the range from about 16, preferably from about 20, to about 26, preferably up to about 24, iv) a mean pore diameter in the range from about 2 nm, preferably 3 nm, to about 12 nm preferably to 9nm, v) a transmission of at least about 70% in the refractive index range of 1.430 to 1.443, and vi) an oil absorption in the range from 70 to 130 cm$^3$/100 g.

After firing at 1100° C. the silicas of the invention had a crystal structure of alpha cristobalite.

These plastics abrasion values correspond to Radioactive Dentine Abrasion (RDA) values of mean 117 (PAV 16) to mean 195 (PAV 26), mean 179 (PAV 24), mean 148 (PAV 20). These were obtained from a correlation between PAV and RDA on 15 silicas having PAV's in the range of 7.5 to 31 with a correlation coefficient of 0.91 (confidence 99%).

Usually the moisture content of the silica will be less than about 25% w/w, preferably less than about 15% w/w.

A transparent toothpaste composition of the invention will contain from about 5% to about 50% by weight, preferably up to about 30%, of an amorphous, precipitated silica of the invention.

Standard Procedures

The silicas of the invention are defined in terms of their physical and chemical properties. The standard test methods used for these properties are:

i) Surface Area

Surface are is determined using standard nitrogen adsorption methods; of Brunauer, Emmett and Teller (BET), using a single point method with a Sorpty 1750 apparatus supplied by Carlo Erba company of Italy. The sample was outgassed under vacuum at 270° C. for 1 hour before measurement.

ii) Oil Absorption

The oil absorption is determined by the ASTM spatula rubout method (American Society of Test Material Standards D, 281).

The test is based upon the principle of mixing linseed oil with a silica by rubbing with a spatula on a smooth surface until stiff putty-like paste is formed which will not break or separate when it is cut with the spatula. The volume of oil used is then put into the following equation:

$$\text{Oil absorption} = \frac{\text{cm}^3 \text{ oil absorption} \times 100}{\text{wt. of silica sample in gms}} = \text{cm}^3 \text{ oil/100 g silica}$$

iii) Weight Mean Particle Size

The weight mean particle size of the silicas is determined with the aid of a Malvern Mastersizer using a 45 nm path length lens. This instrument, made by Malvern Instruments, Malvern, Worcestershire uses the principle of Fraunhöffer diffraction utilising a low power He/Ne laser. Before measurement the sample was dispersed ultrasonically in water for a period of 7 minutes to form a aqueous suspension. The Malvern Mastersizer measures the weight particle size distribution of the silica. The weight mean particle size ($d_{50}$), the 10 percentile ($d_{10}$) and the 90 percentile ($d_{90}$) are easily obtained from the data generated by the instrument.

iv) Plastics Abrasion Value (PAV)

This test is based upon a toothbrush head brushing a Perspex plate in contact with a suspension of the silica in a sorbitol/glycerol mixture. Normally the slurry composition is as follows:

| | |
|---|---|
| Silica | 2.5 grams |
| Glycerol | 10.0 grams |
| Sorbitol Syrup* | 23.0 grams |

*Syrup contains 70% sorbitol/30% water.

All components are weighed into a beaker and dispersed for 2 minutes at 1500 rpm using a simple stirrer. A 110mm× 55mm×3mm sheet of standard clear Perspex is used for the test, supplied by Imperial Chemical Industries PLC under code 000.

The test is carried out using a modified Wet Paint Scrub Tester produced by Research Equipment Limited, Wellington Road, Hampton Hill, Middlesex. The modification is to change the holder so that a toothbrush can be used instead of a paint brush. In addition a weight of 14 ozs is attached to the brush to force the brush onto the Perspex plate.

A Galvanometer is calibrated using a 45° Plaspec gloss head detector and a standard (50% gloss) reflecting plate. The Galvanometer reading is adjusted to a value of 50 under these conditions. The reading of the fresh Perspex plate is then carried out using the same reflectance arrangement.

The fresh piece of Perspex is then fitted into a holder. Two cm$^3$ of the dispersed silica, sufficient to lubricate fully the brushing stroke, is placed on the plate and the brush head lowered onto the plate. The machine is switched on and the plate subjected to three hundred strokes of the weight brush head. The plate is removed from the holder and all the suspension is washed off. It is then dried and re-measured for its gloss value. The abrasion value is the difference between the unabraded value and the value after abrasion.

This test procedure, when applied to known abrasives, gave the following values:

| | Plastics Abrasion Value |
|---|---|
| Calcium carbonate (15 micron) | 32 |
| Silica xerogel (10 micron) prepared by UK 1264292 method | 25 |
| Alumina trihydrate (Gibbsite) (15 micron) | 16 |
| Calcium pyrophosphate (10 micron) | 14 |
| Dicalcium phosphate dehydrate (15 micron) | 7 | v) Electrolyte Levels

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

vi) Moisture Loss at 105° C.

Moisture loss is determined by the loss in weight of a silica when dried to constant weight in an electric oven at 105° C.

vii) Ignition Loss at 1000° C.

Ignition loss is determined by the loss in weight of a silica when ignited in a furnace at 1000° C. to constant weight.

viii) pH

This measurement is carried out on a 5% w/w suspension of the silica in boiled demineralised water ($CO_2$ free).

ix) Crystal Form After Firing at 1100° C.

A sample of the silica is fired in an electric muffle furnace for one hour at 1100° C. The treated sample is allowed to cool and the crystal structure present identified from the trace obtained from an x-ray diffractometer.

x) Mercury intrusion volume:

Mercury intrusion volumes are determined (in cm$^3$/g) by standard mercury intrusion procedures using a Micromeritics Autopore 9220 mercury porosimeter. The pore radius is calculated from the Washburn equation using values of surface tension for mercury of 485 dynes/cm and contact angle of 140°.

Prior to measurement the sample was outgassed at room temperature to a pressure of 50 microns of mercury. The mercury intrusion volume recorded is that occurring over the range of calculated pore diameters of 0.05 to 1.0 micron, when this is shown to represent the true intra-particle porosity of the silica from the mercury intrusion curve, ie. the porosity of the voids within the particles.

Examples 1–5 and 7 have been measured on this basis. An inspection of the intrusion curve for 6 has shown the intrusion volume recorded over the range of calculated pore diameters of 0.05 to 0.2 micron was more appropriate as a true measure of intra-particle porosity.

xi) Apparent Refractive index of silica (RI)/transmission

The sample of silica is dispersed in a range of Sorbitol syrup (70% Sorbitol)/water mixtures. After de-aeration, usually 1 hour, the transmission of the dispersions is determined using a spectrophotometer at 589 nm; water being used as blank. The refractive index of each dispersion is also measured using an Abbe refractometer.

A graphical representation of transmission plotted against refractive index allows the range of refractive indices over which the transmission exceeds 70% to be determined. The maximum transmission of the sample and the apparent refractive index of silica at which this is obtained can also be estimated from this graph.

xii) Mean Pore Diameter (MPD)

This parameter is related to the surface area and pore volume and, using a cylindrical model, is calculated for a silica product with the formula:

$$MPD \text{ (in nm)} = \frac{\text{pore volume (in cm}^3\text{/g)} \times 4000}{\text{surface area (in m}^2\text{/g)}}$$

Pore volume is the mercury intrusion volume defined in (x).

xiii) Radioactive Dentine Abrasion Test (RDA)

The procedure follows the method for assessment of dentifrice abrasivity recommended by the American Dental Association (Journal of Dental Research 55 (4) 563, 1976). In this procedure extracted human teeth are irradiated with a neutron flux and subjected to a standard brushing regime. The radioactive phosphorus 32 removed from the dentin in the roots is used as the index of the abrasion of the dentifrice tested. A reference slurry containing 10g of calcium pyrophosphate in 50 cm$^3$ of 0.5% aqueous solution of sodium carboxymethyl cellulose is also measured and the RDA of this mixture is arbitrarily taken as 100. The precipitated silica to be tested is prepared as a suspension at the same concentration as the pyrophosphate and submitted to the same brushing regime.

xiv) Skeletal Density using Helium Pycnometry

The skeletal density of silica samples is determined using a Micrometrics Accupyc 1330 pycnometer. Before measuring the samples the instrument is calibrated with helium. Sufficient measurements (usually 3) are carried out to allow an accurate calculation of the chamber volume and "dead space" in the apparatus. Measurement of the samples is a repeat of the calibration routine but first the samples are dried at 120° for two hours prior to analysis. The calibrated empty volume of the pycnometer has beeen determined. For each analysis, a sample of known weight is placed in the chamber and the measurement is made automatically.

Specific description of the invention

Examples of the preparation of precipitated silicas will now be given to illustrate but not limit the invention.

A heated stirred reaction vessel was used for the silicate/acid reaction.

Mixing is an important feature in the reaction of silicate and sulphuric acid. Consequently fixed specifications as listed in Chemineer Inc. Chem Eng. 26 April 1976 pages 102–110 have been used to design the baffled heated stirred reaction vessels. Whilst the turbine design is optional to the mixing geometry, a 6-bladed 30° pitched bladed unit has been chosen for our experiments in order to ensure maximum mixing effectiveness with minimum shear. Shear, when required, has been supplied to the reactant mixture by circulating the contents of the reaction vessel through an external high shear mixer (Silverson) containing a square hole high shear screen throughout the simultaneous addition of silicate and acid, or in the case of example 7 throughout the addition of acid I. The energy input being commensurate with the volume flow and number of recirculations required as specified by the manufacturer.

The solutions used in the process were as follows:
i) Sodium silicate solutions having a SiO$_2$:Na$_2$O ratio of in the range of 3.2 to 3.4:1.
ii) A sulphuric acid solution of specific gravity 1.11 (16.1% W/W solution) to 1.15 (21.4 W/W solution).
iii) An electrolyte solution as defined in each example.

The following procedure was adopted in the preparation of the precipitated silicas of the invention. Values of reactant concentrations and volumes, and reaction temperatures are given in Table 1.

(A) liters of water were placed in the vessel together with (B) liters of electrolyte solution and (C) liters of the sodium silicate solution. This mixture was then stirred and heated to (E)° C.

For simultaneous addition routes, (examples 1–6 inclusive), the sodium silicate ((D) liters) and sulphuric acid ((F) liters) solutions were then added simultaneously over a period of about (G) minutes with stirring and if required with shear while maintaining the temperature at (E)° C. The flow rates of the silicate and acid solutions were uniform throughout the addition period to ensure that a constant pH, in the range from about 8.5 to about 10.5, was maintained in the vessel.

In the case of example 7, where all of the silicate was present at the start of the reaction, sufficient sulphuric acid was added over a period of (G) minutes to give a pH 10.5.

In the case of example 6 the slurry was then aged at (E)° C. for (H) minutes.

In all examples sulphuric acid solution (II) was then added over a period of (K) minutes with continued mixing, (but without Silverson shear), to reduce the pH of the slurry to the range of 2.5 to 5.0. During this addition (II) of acid the temperature was maintained at (E)° C.

In examples 1, 4 and 5 a hydrothermal ageing step of (J) minutes at pH 5.0, with the temperature raised to 98° C., was performed during this acid addition II step. Acid II addition subsequent to ageing was begun at this higher temperature but without further heat input. In these examples the pH was reduced to be in the range 2.5 to 4.0 to stop the ageing process.

The resultant slurry was then filtered and washed with water to remove excess electrolyte. Typically, for a toothpaste application, the residual electrolyte would be less than 2% on a dry weight basis. After washing, the filter cake in each example was flash dried, to remove the water rapidly from the silica so that the structure is maintained, and comminuted to the desired particle size range.

The precipitated silicas obtained had the properties, expressed on a dry weight basis listed in Table II.

Example 8

The amorphous silicas prepared as described in examples 1–7 provided satisfactory cleaning properties in the transparent toothpastes in which they were incorporated. The toothpastes had commercially suitable properties for stability and usage. A typical formulation using a silica of this invention is listed below.

| Transparent gel toothpaste | % by weight |
|---|---|
| Sorbosil TC15 | 10.0 |
| Silica of invention | 6.0 |
| Sodium Carboxymethyl Cellulose | 0.7 |
| Sorbitol, 70% non-crystallisable | 61.1 |
| Polyethylene Glycol 1500 | 5.0 |
| Sodium Lauryl Sulphate | 1.5 |
| Sodium Monofluoro-phosphate | 0.8 |
| Flavour | 1.0 |
| Saccharin | 0.2 |
| Colour, Blue, CI42090 | 0.015 |
| Water & minor ingredients | to 100 |
| Properties - Initial Density gcm$^{-3}$ (25° C.) | 1.37 |

Sorbosil TC15 is a thickening silica obtainable from Crosfield Chemicals of Warrington, England.

Example 9

Examples 1 and 2 from EP 0143848 and examples 1, 2 and 3 from EP 0139754 have been repeated. For EP 0143848 (high surface area silicas), Example 1 is a plant batch scale which has to be scaled down, whereas Example 2 is a laboratory scale preparation and, in order to obtain enough sample process, the batch size has been doubled. All the process variables highlighted by this document have been followed. The examples from the low surface area silicas document (EP 0139754) have been repeated according to the teachings of the document.

Table III lists the properties of the silicas of the repetitions together with examples of the present invention. All the amorphous silicas of the prepared examples of the prior art have low plastics abrasion values (below 10) and high oil absorption.

TABLE I

| | Example No. | | | | | | |
|---|---|---|---|---|---|---|---|
| | 1 | 2 | 3 | 4 | 5 | 6 | 7 |
| Vessel capacity (litres) | 64 | 64 | 64 | 64 | 64 | 300 | 64 |
| Water volume (A) (litres) | 7.9 | 18.0 | 13.1 | 9.8 | 9.8 | 68.1 | 12.6 |
| Electrolyte used | NaCl | NaCl | NaCl | NaCl | NaCl | NaCl | NaCl |
| Concentration of electrolyte (% w/w) | 25 | 25 | 25 | 25 | 25 | 25 | 25 |
| Volume of electrolyte (B) (litres) | 6.8 I | 1.7 | 0.9 | 3.8 | 3.8 | 5.1 | 2.4 |
| Silicate weight ratio SiO$_2$/Na$_2$O | 3.22 | 3.30 | 3.29 | 3.25 | 3.22 | 3.28 | 3.26 |
| SiO$_2$ concentration in sodium silicate (% w/w) | 17.39 | 17.49 | 16.52 | 16.77 | 17.39 | 16.61 | 17.41 |
| Silicate volume (C) (litres) | 0.1 | 0.1 | 0.1 | 0.1 | 0.1 | 0.61 | 10.4 |
| Silicate volume (D) (litres) | 9.5 | 14.2 | 11.4 | 11.2 | 10.7 | 60.3 | 0 |
| Acid concentration (% w/w) | 18.1 | 18.5 | 18.1 | 18.2 | 17.8 | 117.5 | 118.0 |
| Acid Volume (F) (litres) | 5.1 | 7.6 | 5.7 | 5.9 | 5.7 | 126.3 | 15.4 |
| Temperature (E) (°C.) | 50 | 80 | 98 | 50 | 50 | 198 | 198 |
| Acid I Additiion time (G) (minutes) | 20 | 20 | 40 | 20 | 20 | 20 | 20 |
| Acid II Addition time (K) (minutes) | 10 | 10 | 10 | 10 | 5 | 10 | 10 |
| Age time (H) (minutes) | 0 | 0 | 0 | 0 | 0 | 10 | 0 |
| Age time (J) (minutes) | 40 | 0 | 0 | 40 | 40 | 0 | 0 |

TABLE II

| | Example No. | | | | | | |
|---|---|---|---|---|---|---|---|
| | 1 | 2 | 3 | 4 | 5 | 6 | 7 |
| Surface Area ($m^2/g$) | 397 | 307 | 262 | 361 | 415 | 145 | 336 |
| Mean Pore Diameter (nm) | 2.9 | 6.0 | 6.9 | 3.1 | 3.0 | 8.2 | 9.6 |
| Plastics Abrasion Value | 23 | 16 | 20 | 22 | 20 | 20 | 16 |
| Maximum Transmission (%) | 83 | 177 | 78 | 76 | 177 | 84 | 71 |
| At Refractive Index of | 1.437 | 1.440 | 1.440 | 1.436 | 1.436 | 1.442 | 1.438 |
| Form After Firing at 1100° C. (*) | Ac | Ac | Ac | Ac | Ac | Ac | Ac |
| Mercury Intrusion Volume ($cm^3/g$) | 0.29 | 0.46 | 0.45 | 0.28 | 0.31 | 0.30 | 0.81 |
| Ignition Loss at 1000° C. (%) | 7.0 | 10.0 | 7.0 | 6.4 | 7.5 | 9.9 | 8.2 |
| Moisture Loss at 105° C. (%) | 0.7 | 5.1 | 2.8 | 1.6 | .2.6 | 3.5 | 3.2 |
| pH | 6.9 | 17.5 | 6.3 | 6.9 | 6.9 | 7.2 | 17.3 |
| Electrolyte Level $SO_4^{2-}$ (%) | 0.08 | 0.05 | 0.11 | 0.10 | 0.06 | 0.11 | 0.05 |
| Electrolyte Level $Cl^-$ (%) | 0.03 | 0.06 | 0.06 | 0.02 | 0.02 | 0.07 | 0.01 |
| Oil Absorption ($cm^3$/100 g) | 80 | 120 | 110 | 75 | 80 | 125 | 110 |
| Paricle size distribution (micron) | | | | | | | |
| 10 percentile | 3.2 | 3.3 | 3.5 | 3.2 | 3.2 | 2.8 | 2.7 |
| 50 percentile | 7.7 | 7.8 | 7.2 | 7.1 | 7.9 | 8.3 | 11.5 |
| 90 percentile | 12.1 | 12.0 | 12.5 | 11.9 | 16.4 | 19.0 | 118.0 |
| Particle greater than | | | | | | | |
| 20 microns (%) | <1.0 | 7.0 | 2.0 | 2.0 | 6.7 | 8.4 | 9.0 |
| 25 microns (%) | <0.1 | <2.0 | <1.0 | <0.1 | 3.7 | 4.4 | 4.6 |
| Helium density ($g/cm^3$) | 2.0764 | 2.0346 | 2.0836 | 2.0943 | 2.0852 | 2.1493 | 2.0448 |

(*) Ac indicates alpha cristobalite

TABLE III

| Examples | BET Surface Area ($m^2/g$) | Oil Absorption ($cm^3/g$) | Apparent Refractive Index | Weight Mean Particle Size (μm) | Plastics Abrasion Value | X-ray phase After Firing 1100° C. |
|---|---|---|---|---|---|---|
| EP0143848 Example 1 | 374 | 170 | 1.459 | 15.0 | 6 | Amorphous |
| EP0143848 Example 2 | 476 | 200 | 1.457 | 16.0 | 3 | Amorphous |
| EP0139754 Example 1 | 24 | 160 | 1.438 | 16.0 | 8 | Amorphous |
| EP0139754 Example 2 | 22 | 175 | 1.448 | 16.6 | 6 | Amorphous |
| EP0139754 Example 3 | 47 | 185 | 1.437 | 16.4 | 3 | Amorphous |
| Invention Example 3 | 262 | 110 | 1.440 | 7.2 | 20 | α cristobalite |
| Invention Example 6 | 145 | 125 | 1.442 | 8.3 | 20 | α cristobalite |

We claim:

1. An amorphous precipitated silica having
   i) a BET surface area in the range from about 100 to 262 $m^2/g$,
   ii) a weight mean particle size in the range 5 microns to 15 microns, with less than 10% of the weight particle size distribution greater than 20 microns,
   iii) a plastics abrasion value in the range from 16 to 26,
   iv) a mean pore diameter in the range from 2 nm to 12 nm,
   v) a transmission of at least about 70% in the refractive index range of 1.430 to 1.443, and
   vi) an oil absorption in the range from 70 to 130 $cm^3$/100 g, said silica being suitable for use as an abrasive in a transparent toothpaste.

2. An amorphous silica according to claim 1 wherein the plastics abrasion value is at least 20.

3. An amorphous silica according to claim 1 wherein the plastics abrasion value is up to 24.

4. An amorphous silica according to claim 1 wherein the oil absorption is at least 115 $cm^3$/100 g.

5. An amorphous silica according to claim 1 wherein the oil absorption is up to 130 $cm^3$/100 g.

6. An amorphous silica according to claim 1 wherein the phase after firing at 1100° C. is alpha-cristobalite.

7. An amorphous silica according to claim 1 with a moisture content of less than about 25% w/w.

8. An amorphous silica according to claim 7 with a moisture content less than about 15% w/w.

9. An amorphous silica according to claim 1 wherein the weight mean particle size is not more than about 12 microns.

10. A transparent toothpaste composition containing from about 5% to about 50% by weight of an amorphous precipitated silica defined in claim 1.

11. A toothpaste composition according to claim 10 which contains from about 5 to about 30% by weight of said silica.

* * * * *